United States Patent [19]
Autant et al.

[11] Patent Number: 4,675,175
[45] Date of Patent: Jun. 23, 1987

[54] COATED METHIONINE GRANULES FOR RUMINANTS

[75] Inventors: Pierre Autant; Andre Cartillier, both of Commentry; Jean-Pierre Quentin, Lyons, all of France

[73] Assignee: A.E.C. Societe De Chimie Organique et Biologique, Commentry, France

[21] Appl. No.: 638,539

[22] Filed: Aug. 7, 1984

Related U.S. Application Data

[63] Continuation of Ser. No. 421,831, Sep. 23, 1982, abandoned.

[30] Foreign Application Priority Data

Oct. 8, 1981 [FR] France ................................. 81 18954

[51] Int. Cl.$^4$ .......................... A61K 9/32; A61K 9/36; A61K 9/22
[52] U.S. Cl. ...................................... 424/33; 424/496; 424/497
[58] Field of Search ....................... 424/33, 35, 14, 19; 524/37, 40, 46

[56] References Cited

U.S. PATENT DOCUMENTS

| 3,303,148 | 2/1967 | Joyner et al. | 524/37 |
| 3,562,806 | 9/1968 | Grant et al. | 424/35 |
| 3,853,988 | 12/1974 | Casadio et al. | 424/22 |
| 3,880,990 | 4/1975 | Bauer et al. | 424/81 |
| 3,978,204 | 8/1976 | Charlé et al. | 424/28 |
| 4,181,709 | 1/1980 | Dannelly | 424/35 |
| 4,196,187 | 4/1980 | Dannelly et al. | 424/35 |

Primary Examiner—Frederick E. Waddell
Attorney, Agent, or Firm—Stevens, davis, Miller & Mosher

[57] ABSTRACT

Composition for coating a biologically active substance, which is stable in a medium of which the pH is greater than or equal to 5, and which permits the release of the active substance in a medium of which the pH is less than or equal to 3.5, and biologically active substances when surrounded by this composition.

7 Claims, No Drawings

COATED METHIONINE GRANULES FOR RUMINANTS

This application is a continuation of application Ser. No. 421,831, filed Sept. 23, 1982, now abandoned.

DESCRIPTION

The present invention relates to a new composition for coating a biologically active substance which is stable in a medium of which the pH is greater than or equal to 5 and which permits the release of the biologically active substance, e.g. a feed or medicament, in a medium of which the pH is less than or equal to 3.5.

In particular, when certain biologically active substances (medicaments, enriched feeds) are administered to ruminants, an enzymatic destruction of these substances, which is favoured by the residence time (a few hours to several days) and by the pH (between 5 and 6), takes place when they pass through the rumen.

It is therefore important to be able to protect these biologically active substances by means of coatings which are stable at a pH which is greater than or equal to 5, i.e. stable in the rumen of the ruminants, which are resistant to degradation by microorganisms and which permit the release of the biologically active substances in part of the digestive system, more particularly in the abomasum, where the pH is less than or equal to 3.5. Whereas the duration of the protection in the rumen must be relatively long (several hours to several days), the release of the active substance must take place in a relatively short time (a few minutes to 1 or 2 hours).

To achieve such a result, it is advantageous to have available polymers which can be used for coating the active substances, and the structure of which is such that they are insoluble in the rumen at a pH of between 5 and 6 but are then soluble, dispersed or highly swollen in the abomasum at a pH of less than 3.5, in order to release the active product.

In this field, it has been proposed to use, inter alia, copolymers of maleic anhydride with another monomer, modified by reaction of a primary/tertiary diamine with the anhydride groups, thus forming aminoimide groups which provide the desired solubility (French Pat. No. 1,536,774). Amino derivatives of cellulose are also known; they are obtained from an unsaturated cellulose derivative (ether, ester) which is reacted with a nitrogen compound containing a mobile hydrogen atom, such as piperidine, morpholine or a secondary amine (French Pat. No. 69/30,562/2,081,320).

Furthermore, British Pat. No. 1,137,214, Australian Pat. No. 454,117, Belgian Pat. No. 865,654 and South African Application No. 70/04,813, and also French Pat. No. 74/33,108/2,246,572 and U.S. Pat. No. 3,341,505, describe copolymers of:

(a) a neutral ethylenic monomer such as methyl acrylate or methacrylate, stryrene, acrylonitrile or vinyl acetate, and (b) an ethylenic monomer carrying a basic nitrogen-containing group, such as diethylaminoethyl acrylate or methacrylate, t-butylaminoethyl acrylate or methacrylate, morpholinoethyl methacrylate or vinylpyridines.

To coat feeds intended for ruminants, it has been proposed to use styrene/vinylpyridine copolymers containing hydrophobic substances chosen from amongst fatty acids containing 12 to 32 carbon atoms or polycarboxylic acids containing 10 to 22 carbon atoms per carboxyl group, which improve the protection by reducing the overall sensitivity of the coating film to aqueous media of weakly acid character (French Pat. No. 78/23,966/2,401,620). In such coating compositions, the hydrophobic substance makes it possible to reduce the wettability of the polymer, but has no effect on the release of the active principle in the acid medium.

It has now been found that a composition suitable for coating a biologically active substance is obtained by associating with a first copolymer which is sensitive to pH variations, a second polymer which is water-insoluble and insensitive to pH variations and, optionally, an organic acid. Release of the active substance at a pH less than or equal to 3.5 is permitted and the second polymer, in particular, improves the release of the active substance at a pH of between 1 and 2.5 and reduces its extractability into an aqueous medium; it is this finding which forms the subject of the present invention.

The present invention accordingly provides a composition for coating a biologically active substance, which is stable in a medium of which the pH is greater than or equal to 5, and which permits the release of the biologically active substance in a medium of which the pH is less than or equal to 3.5, the said composition comprising a copolymer which is sensitive to pH variations and a water-insoluble polymer which is insensitive to pH variations and, optionally, an organic acid.

The copolymer which is sensitive to pH variations is preferably chosen from copolymers of styrene with vinylpyridines such as 2-vinylpyridine, 4-vinylpyridine or alkylvinylpyridines, such as 2-methyl-5-vinylpyridine. Styrene/2-vinylpyridine, styrene/4-vinylpyridine and styrene/2-methyl-5-vinylpyridine are preferred copolymers. In these copolymers, the proportion of styrene is preferably from 5 to 70% by weight and more especially from 5 to 50% by weight, the best results being obtained with copolymers in which the proportion of styrene is from 10 to 40% by weight.

The copolymer used in the coating according to the present invention is preferably characterised by a molecular weight of from 100,000 to 700,000, more especially of from 150,000 to 500,000.

According to the present invention, that polymer forming part of the coating which is insensitive to pH variations possesses the characteristic of being water-insoluble.

Furthermore, it is of no importance whether or not, for example, the water-insoluble polymer is compatible with the styrene/vinylpyridine copolymer. The compatibility can be ascertained from the appearance of a film obtained from a homogeneous solution of a mixture of equal amounts of the copolymer and the polymer: there is incompatibility if the film, when observed with the naked eye, shows the presence of zones corresponding to each of the constituents. Amongst the water-insoluble polymers which can be used for the preparation of the coating composition according to the invention, there may be mentioned: cellulose acetobutyrate, ethylcellulose, cellulose propionate, chlorinated rubber, polycaprolactone or polystyrene. The best results are obtained with cellulose acetobutyrate.

The addition of the water-insoluble polymer to the composition makes it possible to coat active substances using smaller amounts of coating agents whilst at the same time having a coating of suitable quality, in particular if the encapsulation is carried out by the fluidised-bed technique. The amount of coating agent can be up to 50% less than that which would be necessary without the addition of polymer.

The amount of polymer added depends on the sensitivity of the copolymer in an acid medium and on its composition. The water-insoluble polymer preferably represents from 10 to 75% by weight of the mixture of polymers.

When using cellulose acetobutyrate as the water-insoluble polymer, the best results are obtained when the amount of that polymer added represents 20 to 40% by weight of the mixture of polymers.

The addition of the water-insoluble polymer generally leads to the release of a greater amount of the active substance in a medium of which the pH is of the order of 1.5, and makes it possible to obtain a higher proportion of the active substance in the blood of the animals treated.

It has also been found that the coating composition can be improved by incorporating an organic acid, preferably an organic diacid (such as phthalic, oxalic, malonic or succinic acid) or benzoic acid. This optional addition makes it possible to improve the release of the active substance up to pH 3. However, the addition of an acid such as defined above also favours the extraction of the active substance into an aqueous medium. Consequently, the amount of acid added governs the amount of water-insoluble polymer which must be introduced into the composition in order to preserve a low extractability into an aqueous medium and an improvement in the release of the active substance in an acid medium. The amount of acid added is generally up to 50% by weight of the copolymer used.

According to the present invention, other adjuvants can be introduced into the coating composition in order to make it easier to employ by the techniques used. Amongst these adjuvants, there may be mentioned plasticisers such as butyl or octyl phthalate or dibutyl or di-(2-ethylhexyl) adipate, antistatic agents such as quaternary ammonium salts or N-acetylethanolamine, or dyestuffs.

The coating composition is generally obtained by dissolving the copolymer and the water-insoluble polymer in an organic solvent such as tetrahydrofuran or in a mixture or organic solvents such as the mixture acetone/dichloroethane. Other adjuvants can be added to the solution obtained, such as plasticisers or dyestuffs or, in particular when the encapsulation is carried out in a fluidised-air bed, antistatic agents.

The compositions according to the present invention are particularly useful for coating various therapeutic and nutritional substances such as medicaments, vitamins or aminoacids, intended for oral administration to ruminants. These coated substances are generally mixed with the animal feed.

According to a further feature of the present invention there is provided a biologically active substance coated with, or dispersed in, a composition according to the invention.

These coated substances are preferably presented in the form of granules which comprise a central core containing the biologically active substance surrounded by a continuous film of the coating composition. However, the active substances can also be dispersed in the coating composition. In general, the active substance represents 60 to 95% by weight of the granules.

The present invention also relates to the granules consisting of biologically active substances coated with the coating composition.

The granules can be obtained by applying the usual coating techniques such as fluidised-bed encapsulation or coacervation, which make it possible to deposit a continuous film of the coating agent around a core which consists essentially of the active substance and which can be in the form of granules.

The granules obtained should have mechanical properties which are such that they are stable on storage and when handled, such that they do not deteriorate when the animal feeds are being made up, and such that they are not destroyed during their absorption by the animals and, in particular, during mastication by crushing or grinding.

The size of the granules will depend on the way in which they are to be used and will be determined more particularly by the animal for which they are intended. It is preferable to coat particles having a size of between 0.5 and 5 mm in order to obtain granules of an appropriate size.

Of very particular value are the granules which contain methionine as the active principle, methionine playing a very important part in the feeding of animals and, more particularly, ruminants.

The Examples which follow illustrate coating compositions according to the invention and their use for the preparation of coated active substances.

In the Examples, the properties of the products are determined from the following tests:

(1) extraction into an acid medium in vitro:

The product to be studied (0.5 g) is incubated for 15 minutes, 30 minutes or 1 hour in KCL/HCL medium (50 cc) which has been brought to the desired pH (1.5 or 3) beforehand and which is kept, without stirring, in a thermostatically controlled bath at 40° C.

When the incubation time has elapsed, the extraction liquid is filtered. The dissolved active product is determined by a suitable method. The ratio of this value to the amount of product initially introduced gives the degree of release.

In the case where the active substance is methionine, the dissolved methionine is determined quantitatively by iodometry using the method in "New and Non-Official Remedies", Lippincott (1952).

(2) resistance in the rumen:

Samples of granules to be studied (about 0.5 g) are introduced into nylon sachets having a mesh size of $300 \times 300\mu$. The sachets are incubated for 48 hours in the rumen of fistulous ewes. The sachets are then recovered and washed. The remaining active substance is quantitatively determined by a suitable method.

(3) determination of the blood levels:

The relative efficacy of different products is measured by their ability to raise the level of active substance in the blood during standardised supplementation tests.

In the case of methionine, doses containing 6 g of methionine equivalent are administered directly, twice daily, into the rumen of fistulous ewes. This supplementation diet is maintained for 7 days and blood samples are taken on the 6th and 7th days. The methionine is determined on whole blood, the quantitative analysis being carried out by the method of STEIN and MOORE.

In order to check the difference of efficacy of two formulations, crossover tests are carried out on several animals. After each supplementation period, a control period of 7 days is allowed to elapse without providing active substance, at the end of which period a check is carried out to ensure that the blood level has returned to its initial value.

EXAMPLE 1

Granular methionine (400 g), in the form of spherical particles containing 98% of methionine and having a diameter of between 0.5 and 0.63 mm, is coated, by the fluidised-bed technique, with a coating agent (72 g) consisting of 70 parts of 2-vinylpyridine/styrene copolymer (70/30) and 30 parts of cellulose acetobutyrate.

This gives granules having the following characteristics:
methionine content: 75.9%
extractable into water:
 15.4% after 16 hours
 23.7% after 48 hours
resistance in the rumen: 78.8% after 48 hours
extractable into an acid medium at pH 1.5:
 71% after 15 minutes
 98% after 30 minutes
 100% after 1 hour By way of comparison, granules prepared from methionine (400 g) and 2-vinylpyridine/styrene copolymer (72 g) have the following characteristics:
methionine content: 73%
extractable into water:
 20.3% after 16 hours
 31.3% after 48 hours
resistance in the rumen: 70% after 48 hours
extractable into an acid medium at pH 1.5:
 42% after 15 minutes
 71% after 30 minutes
 85% after 1 hour The granules obtained according to the present invention were tested on fistulous ewes. The coated methionine is introduced into the rumen via the fistula. The animals receive a dose of 6 g/day or 12 g/day for 5 days and then in the following week the animals receive nothing (control week). The methionine absorbed is estimated by measuring the accumulation in the blood at the end of the week. The blood methionine level is expressed in mg of methionine per 100 g of blood. At a dose of 6 g/day, the blood level is 6.9 mg/100 g of blood, and at a dose of 12 g/day, it is 13.4 mg/100 g of blood, whereas, when the methionine is administered in the uncoated form, the blood levels are respectively 1.32 and 1.61 mg per 100 g of blood.

Consequently, the blood methionine level is 8.3 times greater at a dose of 12 g/day and 5.3 times greater at a dose of 6 g/day.

The coating composition is prepared in the following manner:

2-Vinylpyridine/styrene copolymer (70/30) (50.4 g) and cellulose acetobutyrate (21.6 g) are dispersed in tetrahydrofuran (1,200 cc), and butyl phthalate (1.5 g) and dyestuff (0.07 g) are then added.

When the dissolution is complete, N-acetylethanolamine is added in a sufficient amount for the resistivity of the solution to be less than or equal to $10^6$ Ωcm.

This solution is then sprayed onto the methionine to be coated, in an apparatus which permits coating in a fluidised-air bed.

The 2-vinylpyridine/styrene copolymer used in the preparation of the coating agent is obtained in the following manner:

In a 25 liter reactor, methylcellulose (14 g) is dissolved in distilled water (9,334 g). The solution is heated to 60° C. and a mixture of styrene (1,200 g), 2-vinylpyridine (2,800 g) and azo-bis-isobutyronitrile (40 g) is then added, with stirring at a speed of 150 rpm.

The stirring and the temperature (60°–63° C.) are maintained for 4 hours 30 minutes. The suspension is then filtered. The polymer collected is washed with distilled water and then dried to constant weight at 60° C. under reduced pressure (100 mm Hg; 13.3 kPa).

This gives styrene/2-vinylpyridine copolymer (28.6/71.4) (3.630 kg), which has a specific viscosity of 0.520 (determination at a concentration of 5 g/liter in dimethylformamide solution at 23° C.) and which has a weight-average molecular weight of the order of 410,000.

The degree of polymerisation is 91%.

The cellulose acetobutyrate has the following characteristics:
Average molecular weight: 57,000
Number of groups per cellulose unit:
 acetate: 1.2
 butyrate: 1.8

EXAMPLE 2

The procedure of Example 1 is followed, but using 1,200 g of granular methionine containing about 98% of methionine; this gives granules having the following characteristics:
methionine content: 77.5%
extractable into water at 20° C.:
 10.7% after 16 hours
 21.5% after 48 hours
resistance in the rumen: 84.1% after 48 hours
extractable into an acid medium at pH 1.5:
 94% after 15 minutes
 98% after 30 minutes
 100% after 1 hour These granules are subjected to a mastication test in fistulous ewes. The protected methionine is administered for 1 week into the fistula and for 1 week by addition to the concentrated feed. Between these two weeks, there is a week corresponding to a control period (absence of the methionine supplementation).

The difference in the blood methionine level is due to the action of the mastication. A 13 to 15% reduction in the blood methionine level is thus recorded.

The granules thus obtained are tested in the preparation of a 0.2% feed for chicks (preparation of 100 kg of feed in a "GONDARD" mixer). The percentage of water-extractable methionine in the feed manufactured corresponds to that obtained for the initial coated methionine; in fact, in 2 hours, the percentage of water-extractable methionine (relative to the methionine present) represents 3.8% for the feed, whereas it is 4.4% for the initial coated methionine.

EXAMPLE 3

Granular methionine (400 g), in the form of spherical particles containing 98% of methionine and having a diameter of between 0.5 and 0.63 mm, is coated, by the fluidised-bed technique, with a coating agent (120 g) consisting of 70 parts of 2-vinylpyridine/styrene copolymer (70/30) and 30 parts of cellulose acetobutyrate.

Furthermore, a control product in which the coating agent consists of 100% of 2-vinylpyridine/styrene copolymer (70/30) is prepared under the same conditions.

This gives granules having the following characteristics:

|  | Coated product containing cellulose acetobutyrate | Control |
| --- | --- | --- |
| Methionine content | 66.0% | 62.5% |
| Extractable into water |  |  |
| - after 16 hours | 5.8% | 7.1% |
| - after 48 hours | 9.1% | 19.1% |
| Resistance in the rumen | 90% | 86% |
| - after 48 hours |  |  |
| Extractable into an acid medium at pH 1.5 |  |  |
| - after 15 minutes | 58% | 24% |
| - after 30 minutes | 85% | 45% |
| - after 1 hour | 100% | 47% |
| Methioninaemia (12 g/day × 7 days) in mg of methionine/100 g of blood |  |  |
| Ewe A | 12.0 | 7.1 |
| B | 16.0 | 6.4 |
| C | 13.3 | 3.1 |
| D | 12.4 | 6.0 |
| E | 10.2 |  |
| F |  | 1.8 |
| G |  | 5.4 |

EXAMPLE 4

Granular methionine (400 g), in the form of spherical particles containing 98% of methionine and having a diameter of between 0.5 and 0.63 mm, is coated, by the fluidised-bed technique, with a coating agent (87.1 g) consisting of 57.9 parts of 2-vinylpyridine/styrene copolymer (70/30), 24.8 parts of cellulose acetobutyrate and 17.3 parts of phthalic acid.

This gives granules having the following characteristics:
methionine content: 75%
extractable into water at 20° C.:
  11.3% after 16 hours
  17.8% after 48 hours
resistance in the rumen: 72.3% after 48 hours
extractable into an acid medium at pH 1.5:
  42% after 15 minutes
  70% after 30 minutes
  90% after 1 hour
extractible into an acid medium at pH 3:
  9% after 15 minutes
  16% after 30 minutes
  20% after 1 hour

EXAMPLE 5

Granular methionine (400 g), in the form of spherical particles containing 98% of methionine and having a diameter of between 0.5 and 0.63 mm, is coated, by the fluidised-bed technique, with a coating agent (80 g) consisting of 70 parts of 2-vinylpyridine/styrene copolymer (70/30), 20 parts of cellulose acetobutyrate and 10 parts of phthalic acid.

This gives granules having the following characteristics:
methionine content: 66.3%
extractable into water:
  5.2% in 16 hours
  8.3% in 48 hours
resistance in the rumen: 64.0% after 48 hours
extractable into an acid medium at pH 1.5:
  77.0% after 15 minutes
  95.0% after 30 minutes
  100% after 1 hour
extractable into an acid medium at pH 3:
  10.5% after 15 minutes
  16% after 30 minutes
  28% after 1 hour By way of comparison, a product coated with the 2-vinylpyridine/styrene copolymer (70/30) by itself, under the conditions described in Example 1, has a proportion extractable at pH 3 of:
  6% after 15 minutes
  8% after 30 minutes
  15% after 1 hour.

EXAMPLE 6

Granular methionine (400 g), in the form of spherical particles having a diameter of between 0.5 and 0.63 mm and containing 98% of methionine, is coated with a coating agent (72 g) consisting of 70 parts of 2-vinylpyridine/styrene copolymer (90/10) and 30 parts of cellulose acetobutyrate, the process being carried out in a fluidised bed.

This gives granules having the following characteristics:
methionine content: 72.2%
extractable into water:
  11.8% in 16 hours
  24.5% in 48 hours
resistance in the rumen: 85.5% after 48 hours
extractable into an acid medium at pH 1.5:
  85.6% after 15 minutes
  100% after 30 minutes
  100% after 1 hour
extractable into an acid medium at pH 3:
  5% after 15 minutes
  15% after 30 minutes
  26% after 1 hour

EXAMPLE 7

Granular methionine (400 g), in the form of spherical particles having a diameter of between 0.5 and 0.63 mm and containing about 98% of methionine, is coated with a coating agent (120 g) consisting of a mixture of 67 parts of a 2-methyl-5-vinylpyridine/styrene copolymer (77.4/22.6) and 33 parts of ethylcellulose, the process being carried out in a fluidised bed.

This gives granules having the following characteristics:
methionine content: 66.2%
extractable into water:
  11.3% in 16 hours
  20.1% in 48 hours
resistance in the rumen: 84% after 48 hours
extractable into an acid medium at pH 1.5:
  27% after 15 minutes
  50% after 30 minutes
  66% after 1 hour By way of comparison, granules prepared from methionine (400 g) and 2-methyl-5-vinylpyridine/styrene copolymer (120 g) have the following characteristics:
methionine content: 62.9%
extractable into water:
  14.5% after 16 hours
  20.1% after 48 hours
extractable into an acid medium at pH 1.5:
  18% after 15 minutes
  35% after 30 minutes
  48% after 1 hour The 2-methyl-5-vinylpyridine/styrene copolymer (77/23) can be prepared in the following manner:

In a 25 liter reactor, methylcellulose (17.5 g) is dissolved in distilled water (11,667 g). The solution is heated to 60° C. and a mixture of styrene (1,050 g), 2-methyl-5-vinylpyridine (3,950 g) and azo-bis-isobutyronitrile (50 g) is then added. After heating for 4 hours 30 minutes at 63° C., with stirring at a speed of 150 rpm, the polymer has solidified. Dimethylformamide (7 liters) is added after the supernatant liquid has been drawn off.

The solution obtained is poured into water at a rate of 1 liter of solution per 10 liters of water. The polymer precipitated is filtered off, washed with distilled water and dried to constant weight at 60° C. under reduced pressure (100 mm Hg; 13.3 kPa).

This gives 5-methyl-2-vinylpyridine/styrene copolymer (77.3/22.6) (4,200 g), the specific viscosity of which is 0.486 (determination at a concentration of 5 g/liter in dimethylformamide solution at 20° C.).

The degree of polymerisation is 84%.

We claim:

1. A coated methionine granule for oral administration to a ruminant which is stable in a medium of which the pH is greater than or equal to 5, and which permits the release of the methionine in a medium of which the pH is less than or equal to 3.5, and wherein said coating comprises a copolymer which is sensitive to pH variations selected from the group consisting of a copolymer of styrene and 2-vinylpyridine, a copolymer of styrene and 4-vinylpyridine, and a copolymer of styrene and 2-methyl-5-vinylpyridine, the proportion of styrene in the copolymer being from 5 to 70% by weight, and a water-insoluble polymer which is insensitive to pH variations selected from the group consisting of cellulose acetobutyrate, ethylcellulose, and cellulose propionate, the proportion of water-insoluble polymer being from 10 to 75% by weight of the mixture of polymers, and wherein the methionine is present in an amount such that the coated granule has a methionine content of from 60 to 95% by weight.

2. A coated methionine granule according to claim 1, wherein the proportion of styrene in the polymer is from 5 to 50% by weight.

3. A coated methionine granule according to claim 1, wherein the proportion of styrene in the polymer is from 10 to 40% by weight.

4. A coated methionine granule according to claim 1, wherein the copolymer has a molecular weight of from 100,000 to 700,000.

5. A coated methionine granule according to claim 1, wherein the copolymer has a molecular weight of from 150,000 to 500,000.

6. A coated methionine granule according to claim 1 in which the water-insoluble polymer is cellulose acetobutyrate.

7. A coated methionine granule according to claim 6, wherein the cellulose acetobutyrate represents 20 to 40% by weight of the mixture of polymers.

* * * * *